United States Patent [19]

Mazzagatti

[11] 4,429,273
[45] Jan. 31, 1984

[54] OIL-WATER MONITOR

[75] Inventor: Roy P. Mazzagatti, Bellaire, Tex.

[73] Assignee: Texaco Inc., White Plains, N.Y.

[21] Appl. No.: 245,863

[22] Filed: Mar. 20, 1981

[51] Int. Cl.³ ..................... G01R 27/04; G01R 27/26
[52] U.S. Cl. ............................ 324/61 R; 324/58.5 R; 73/61.1 R
[58] Field of Search ................. 73/61.1 R; 324/61 R, 324/65 R, 58.5 R, 445

[56] References Cited

U.S. PATENT DOCUMENTS

| 4,266,188 | 5/1981 | Thompson | 324/61 R X |
| 4,336,493 | 6/1982 | Gregory et al. | 324/61 R |
| 4,367,440 | 1/1983 | Mazzagatti | 324/445 |

FOREIGN PATENT DOCUMENTS 193617 3/1967 U.S.S.R. ........................... 324/61 R
725008 3/1980 U.S.S.R. ........................... 324/61 R

OTHER PUBLICATIONS

Chamberlain et al.; "Dielectric Constant Continuous Analyzer in Petroleoum Refining"-*Industrial and Engineering Chemistry*-Nov., 1956.

Primary Examiner—Stanley T. Krawczewicz
Assistant Examiner—Jose M. Solis
Attorney, Agent, or Firm—Carl G. Ries; Robert A. Kulason; Ronald G. Gillespie

[57] ABSTRACT

An oil-water monitor includes a test cell having a production stream passing through it, thereby allowing the dielectric properties of the production stream to be monitored. An analyzer connected to the measuring cell provides an indication of the water content of the production stream in accordance with the dielectric properties of the production stream.

7 Claims, 1 Drawing Figure

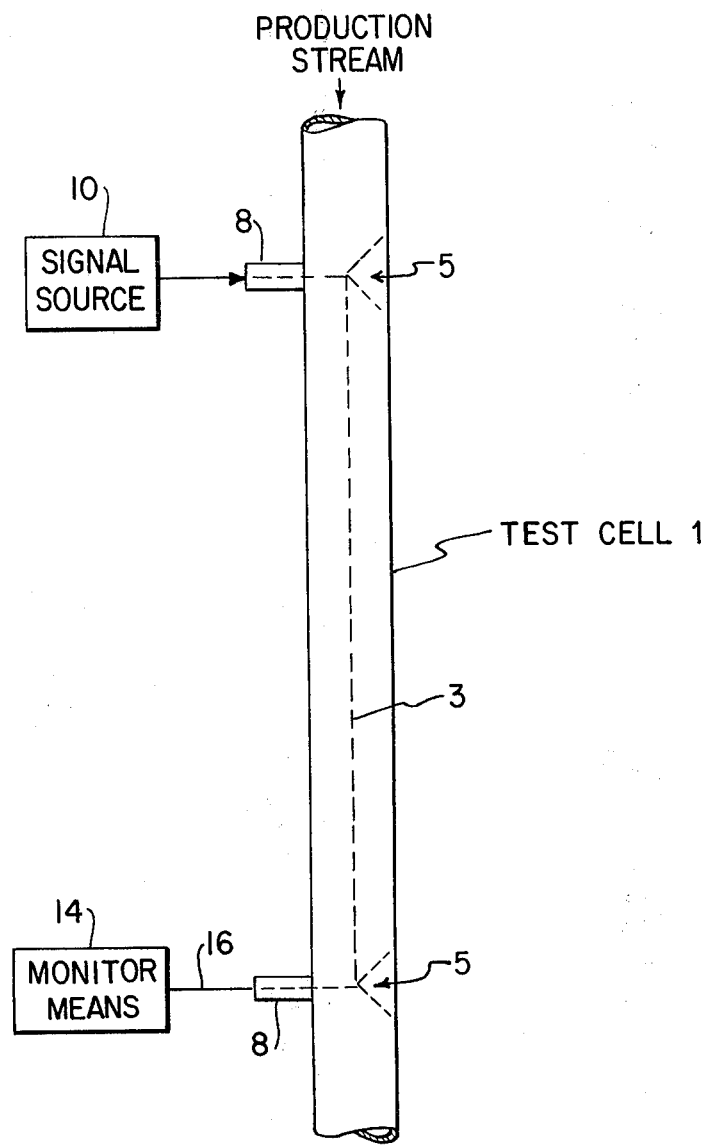

OIL-WATER MONITOR

BACKGROUND OF THE INVENTION

1. Field of the Invention

The present invention relates to monitors in general and, more particularly, to monitors used in the petroleum industry.

2. Summary of the Invention

An oil-water monitor includes a test cell through which passes a production stream in such a manner that the dielectric properties of the production stream may be monitored. An analyzer provides an indication of the water content of the production stream in accordance with the dielectric properties of the production stream.

The objects and advantages of the present invention will appear more fully hereinafter from a consideration of the detailed description which follows, taken together with the following drawing wherein one embodiment of the invention is illustrated by way of example. It is to be expressly understood, however, that the drawing is for illustration purposes only and is not to be construed as defining the limits of the invention.

DESCRIPTION OF THE DRAWING

The drawing is a partial schematic and in partial simplified block diagram of an oil-water monitor constructed in accordance with the present invention.

DESCRIPTION OF THE INVENTION

The present state of the art using a capacitance probe to determine the basic sediment and water (BS&W) content of crude oils requires that the fluid in the stream does not contain free water, or if it does that the free water be bypassed past the capacitance probe. This requirement imposes undesirable and expensive constraints upon such an installation.

For the purpose of the present invention, the flowing fluid from an oil well is referred to as the "production stream."

Generally speaking, there are three conditions that production streams may be in. One condition is the water-in-oil condition, that is where the water is trapped in the oil requiring the use of special monitors to determine the water content. However, there is no known monitor for a second condition, the oil-in-water condition, that is where the percentage of water is so great that the oil readily separates from the water and the separated oil does not contain water in any substantial amounts. There is a third condition which is really a combination of the first two conditions, namely there is separated water, however the separated oil may contain substantial amounts of trapped water. There are no clearly defined physical boundaries between the three conditions. The production stream changes from the water-in-oil condition through the oil-in-water condition as the percentage of water increases. The operator may not know the condition of the production stream or the condition of the production stream may change during production. The present invention not only monitors the oil-in-water condition but also is applicable to the water-in-oil condition and to the third condition.

The present invention avoids the problem of free water by utilizing a test cell 1, made of electrically conductive material, passing a production stream. Cell 1 has an electrical conductor 3, which may be a wire or even a small diameter pipe, arranged along its longitudinal axle and which is supported by insulator supports 5. Conductor 3 is connected at both ends to coaxial type connectors 8. Thus, cell 1 and conductor 3 form in effect an electrical coaxial transmission line of a predetermined length. The dielectric material for that portion forming the coaxial line is the production stream flowing through cell 1.

A signal source 10 may provide either a continuous wave electrical signal having a frequency within a preferable range of 100 kilohertz to 500 megahertz or may be an electrical pulse having a duration of 1 nanosecond or greater. The signal, after being transmitted through test cell 1, is provided to monitor means 14 by way of a coaxial line 16. It is not necessary to know the details of monitor means 14 to understand the present invention except to say that within monitor means 14 there are provisions for providing reference voltages corresponding to the signal provided by signal source 10 after transmission through various mixes of production streams. Monitor means 14 then compares the signal during a test with the references and provides an indication of the percentage of water in the production stream.

In another embodiment of the present invention, signal source 10 and monitor means 14 may be omitted and an impedance analyzer, which may be of the type manufactured by Hewlett Packard, Model 4191A RF Impedance Analyzer, used. It is only necessary to connect one of the connectors 8 to the impedance analyzer. It can be appreciated that as the dielectric of coaxial test cell 1 changes, its impedance characteristic changes accordingly, thus allowing the impedance to be measured by the analyzer which may then be correlated with the water content of the production stream.

The present invention as hereinbefore described is an oil-water monitor capable of monitoring the water content in a production stream regardless of whether the stream contains free water or not. The monitor includes a test cell which, in effect, is an electrical coaxial transmission line of a predetermined length whose dielectric material between the inner conductor and the outer conductor is the production stream whose dielectric properties change in accordance with the composition of the production stream.

What is claimed is:

1. An oil-water monitor which monitors a production stream comprising
    cell means for having the production stream pass through it in such a manner that the dielectric properties of the production stream may be monitored, regardless of whether the production stream is in a water-in-oil condition, an oil-in-water condition or a combination of the two conditions, and
    means connected to said cell means for providing an indication of the water content of the production stream in accordance with the dielectric properties of the production stream.

2. A monitor as described in claim 1 in which the cell means is coaxial conductive means having an inner conductive means and an outer conductive means, and the dielectric material separating the two conductive means is the production stream.

3. A monitor as described in claim 2 in which
    the outer conductive means is a metallic pipe through which the production stream flows, and
    the inner conductive means is a wire conductor; and further comprising means for supporting said inner conductor along the long longitudinal axis of the pipe, and at least one connector means for providing external electric coaxial connection for the conductor and the pipe to the indicating means.

4. A monitor as described in claim 3 in which said indicator means includes a signal source providing an electrical signal to one connection means, and monitor means connected to another connection means for monitoring the electrical signal after transmission through the cell means.

5. A monitor as described in claim 4 in which the electrical signal is a continuous wave signal having a predetermined frequency in the range of 100 kilohertz to 500 megahertz.

6. A monitor as described in claim 4 in which the electrical signal is a pulse signal in which each pulse has a predetermined duration greater than 1 nanosecond.

7. A monitor as described in claim 3 in which said indicating means is an impedance analyzer connected to the connector means which measures the impedance of the cell means with the production stream flowing through said cell means.

* * * * *